US011560271B2

(12) United States Patent
Sheng

(10) Patent No.: US 11,560,271 B2
(45) Date of Patent: Jan. 24, 2023

(54) LIQUID CONTAINERS FOR ELECTRONIC SMOKING DEVICE

(71) Applicant: FONTEM HOLDINGS 1 B.V., Amsterdam (NL)

(72) Inventor: Min Sheng, Beijing (CN)

( * ) Notice: Subject to any disclaimer, the term of this patent is extended or adjusted under 35 U.S.C. 154(b) by 47 days.

(21) Appl. No.: 16/931,083

(22) Filed: Jul. 16, 2020

(65) Prior Publication Data

US 2020/0345065 A1 Nov. 5, 2020

Related U.S. Application Data

(62) Division of application No. 15/744,031, filed as application No. PCT/CN2015/085058 on Jul. 24, 2015, now abandoned.

(51) Int. Cl.

| | |
|---|---|
| ***A24F 40/42*** | (2020.01) |
| ***B65D 85/00*** | (2006.01) |
| ***B05B 7/24*** | (2006.01) |
| ***B05B 7/16*** | (2006.01) |
| ***A24F 40/30*** | (2020.01) |
| ***A24F 40/44*** | (2020.01) |

(Continued)

(52) U.S. Cl.

CPC .............. *B65D 85/70* (2013.01); *A24F 40/30* (2020.01); *A24F 40/42* (2020.01); *A24F 40/44* (2020.01); *B05B 7/1686* (2013.01); *B05B 7/2472* (2013.01); *H05B 1/0297* (2013.01); *A24F 40/10* (2020.01)

(58) Field of Classification Search

CPC .......... A24F 40/30; A24F 40/40; A24F 40/42; A24F 47/008; A24F 40/10

See application file for complete search history.

(56) References Cited

U.S. PATENT DOCUMENTS 9,861,135 B2 1/2018 Chen
2011/0226236 A1* 9/2011 Buchberger .......... A24F 40/485 128/200.23
2011/0232654 A1 9/2011 Mass et al.

(Continued)

FOREIGN PATENT DOCUMENTS

CN 201209033 Y 3/2009
CN 202068930 U 12/2011

(Continued)

OTHER PUBLICATIONS

CN103960785 (Machine Translation) [online], [retrieved on Oct. 18, 2021], retrieved from Google Patents (https://patents.google.com/) (Year: 2014).*

(Continued)

*Primary Examiner* — Michael J Felton
*Assistant Examiner* — Yana B Krinker
(74) *Attorney, Agent, or Firm* — Perkins Coie LLP; Kenneth H. Ohriner

(57) ABSTRACT

An electronic smoking device includes a liquid supply (34) and an atomizer in a housing. The liquid supply (34) includes at least two container members (34*a*, 34*b*) attachable to one another through a connection mechanism to form a liquid supply main body. Each of the container members (34*a*, 34*b*) may have an outlet (341*a*, 341*b*) sealed by a sealing member (342*a*, 342*b*) and a second end which is closed, and an aerosol channel (343*a*, 343*b*) formed between the container members.

14 Claims, 7 Drawing Sheets

(51) Int. Cl.
*H05B 1/02* (2006.01)
*A24F 40/10* (2020.01)

(56) References Cited

U.S. PATENT DOCUMENTS

| | | | |
|---|---|---|---|
| 2013/0213418 | A1 | 8/2013 | Tucker et al. |
| 2014/0261490 | A1 | 9/2014 | Kane et al. |
| 2014/0261493 | A1 | 9/2014 | Smith et al. |
| 2015/0144145 | A1 | 5/2015 | Chang et al. |
| 2016/0029699 | A1 | 2/2016 | Yu et al. |

FOREIGN PATENT DOCUMENTS

| | | | | |
|---|---|---|---|---|
| CN | 202233007 | U | 5/2012 | |
| CN | 103960785 | A | 8/2014 | |
| CN | 203828070 | U | 9/2014 | |
| CN | 104114050 | A | 10/2014 | |
| CN | 203934988 | U | 11/2014 | |
| CN | 204070555 | U | 1/2015 | |
| GB | 2504076 | A | 1/2014 | |
| JP | H0271707 | A | 3/1990 | |
| KR | 20080067474 | A | 7/2008 | |
| WO | 02087395 | A1 | 11/2002 | |
| WO | 2012040788 | A1 | 4/2012 | |
| WO | 2015038981 | A2 | 3/2015 | |
| WO | WO-2015117702 | A1 * | 8/2015 | ............ A61M 15/06 |

OTHER PUBLICATIONS

European Patent Office, Extended European Search Report for European Application No. 15899143.0; dated Jun. 18, 2018; 14 pages.
State Intellectual Property Office, First Office Action in Chinese Application No. 201580083011.3 with English translation; dated Nov. 11, 2019; 25 pages.
State Intellectual Property Office, International Search Report and Written Opinion for PCT/CN2015/085058,dated Apr. 27, 2016, 12 pgs.
European Patent Office, First Office Action in European Application No. 15899143.0 dated Oct. 7, 2020; 12 pages.
State Intellectual Property Office, Second Office Action in Chinese Application No. 201580083011.3 with English translation summary; dated May 25, 2020; 9 pages.
State Intellectual Property Office, Decision of Rejection in Chinese Application No. 201580083011.3 with English translation summary; dated Nov. 18, 2020; 6 pages.

* cited by examiner

LIQUID CONTAINERS FOR ELECTRONIC SMOKING DEVICE

CROSS-REFERENCE TO RELATED APPLICATION(S)

This application is a Division of U.S. application Ser. No. 15/744,031 filed Jan. 11, 2018 and now pending, which is a 371 of PCT/CN2015/085058 filed Jul. 24, 2015. These applications are incorporated herein by reference.

TECHNICAL FIELD

The invention relates to liquid supply of an electronic smoking device, such as an electronic cigarette or vaporizing device. More particularly the invention relates to an electronic smoking device having a liquid supply with more than one type or flavor of e-liquid.

BACKGROUND

Many electronic smoking or vaporizing devices use an open tank system which allows the tank holding the liquid supply to be opened and refilled by the user. However, open tank systems allow any liquid to be used, which has disadvantages. Refilling also risks the liquid contacting the users hands, which is otherwise better avoided. Other electronic vaporizing devices use a closed system, where the device is either not refillable, or is refillable using a closed or sealed container, which is opened only upon installation of the container into the device. Although the closed systems avoid many of the disadvantages of the open systems, engineering challenges remain in designing liquid containers for electronic smoking or vaporizing devices that are conveniently and easily used, and which may also allow for simultaneous use of more than one type of liquid.

SUMMARY OF THE INVENTION

An electronic smoking device includes a liquid supply and an atomizer in a housing. The liquid supply includes at least two container members attachable to one another through a connection mechanism to form a liquid supply main body. Each of the container members may have a first end sealed by a sealing member and a second end which is closed, and an aerosol channel formed between the container members.

DETAILED DESCRIPTION

Electronic Cigarettes in General

Figure 5:
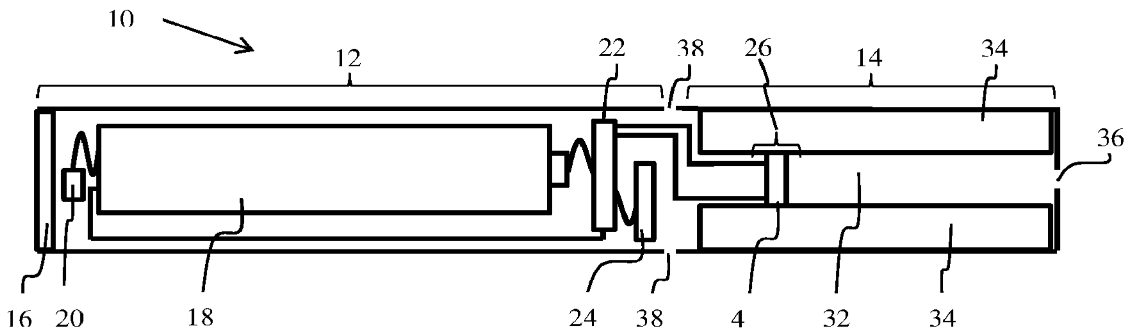
FIG. 5 is a schematic diagram of an electronic cigarette or smoking device.

As shown in FIG. 5, an e-cigarette 10 typically has a housing comprising a cylindrical hollow tube having an end cap 16. The cylindrical hollow tube may be single piece or a multiple piece tube. In FIG. 5 the cylindrical hollow tube is shown as a two piece structure having a battery portion 12 and an atomizer/liquid reservoir portion 14. Together the battery portion 12 and the atomizer/liquid reservoir portion 14 form a cylindrical tube which is approximately the same size and shape as a conventional cigarette, typically about 100 mm with a 7.5 mm diameter, although lengths may range from 70 to 150 or 180 mm, and diameters from 5 to 20 mm.

The battery portion 12 and atomizer/liquid reservoir portion 14 are typically made of metal or plastic and act together with the end caps to provide a housing to contain the components of the e-cigarette 10. The battery portion 12 and the atomizer/liquid reservoir portion 14 may be configured to fit together by a friction push fit, a snap fit, or a bayonet attachment, magnetic fit, or screw threads. The end cap 16 is provided at the front end of the battery portion 12. The end cap 16 may be made from translucent plastic or other translucent material to allow an LED 20 positioned near the end cap to emit light through the end cap.

An air inlet may be provided in the end cap, at the edge of the end cap next to the cylindrical hollow tube, anywhere along the length of the cylindrical hollow tube, or at the connection of the battery portion 12 and the atomizer/liquid reservoir portion 14. FIG. 5 shows a pair of air inlets 38 provided at the intersection between the battery portion 12 and the atomizer/liquid reservoir portion 14.

A battery 18, a light emitting diode (LED) 20, control electronics 22 and optionally an airflow sensor 24 are provided within the cylindrical hollow tube battery portion 12. The battery 18 is electrically connected to the control electronics 22, which is electrically connected to the LED 20 and the airflow sensor 24. In this example the LED 20 is at the front end of the battery portion 12, adjacent to the end cap 16 and the control electronics 22 and airflow sensor 24 are provided at the other end of the battery portion 12, adjacent the atomizer/liquid reservoir portion 14.

The airflow sensor 24 acts as a puff detector, detecting a user puffing or sucking on the atomizer/liquid reservoir portion 14 of the e-cigarette 10. The airflow sensor 24 can be any suitable sensor for detecting changes in airflow or air pressure such a microphone switch including a deformable membrane which is caused to move by variations in air pressure. Alternatively the sensor may be a Hall element or an electro-mechanical sensor.

The control electronics 22 are also connected to an atomizer 26. In the example shown, the atomizer 26 includes a heating coil 28 which is wrapped around a wick 30 extending across a central passage 32 of the atomizer/liquid reservoir portion 14. The coil 28 may be positioned anywhere in the atomizer and may be transverse or parallel to the liquid reservoir. The wick 30 and heating coil 28 do not completely block the central passage 32. Rather an air gap is provided on either side of the heating coil 28 enabling air to flow past the heating coil 28 and the wick 30. The atomizer may alternatively use other forms of heating elements, such as ceramic heaters, or fiber or mesh material heaters. Nonresistance heating elements such as sonic, piezo and jet spray may also be used in the atomizer in place of the heating coil.

The central passage 32 is surrounded by a cylindrical liquid supply 34 with the ends of the wick 30 abutting or extending into the liquid supply 33. The wick 30 may be a porous material such as a bundle of fiberglass fibers, with liquid in the liquid supply 33 drawn by capillary action from the ends of the wick 30 towards the central portion of the wick 30 encircled by the heating coil 28.

The liquid supply 33 may alternatively include wadding soaked in liquid which encircles the central passage 32 with the ends of the wick 30 abutting the wadding. In other embodiments the liquid supply 33 may comprise a toroidal cavity arranged to be filled with liquid and with the ends of the wick 30 extending into the toroidal cavity.

An air inhalation port 36 is provided at the back end of the atomizer/liquid reservoir portion 14. The inhalation port 36 may be formed in the cylindrical hollow tube atomizer/liquid reservoir portion 14 or may be formed in a separate mouthpiece attached to the atomizer/liquid reservoir portion 14.

In use, a user sucks on the e-cigarette 10. This causes air to be drawn into the e-cigarette 10 via one or more air inlets, such as air inlets 38 and to be drawn through the central passage 32 towards the air inhalation port 36. The change in air pressure is detected by the airflow sensor 24 which generates an electrical signal that is passed to the control electronics 22. In response to the signal, the control electronics 22 activates the heating coil 28 which causes liquid present in the wick 30 to be vaporized creating an aerosol (which may comprise gaseous and liquid components) within the central passage 32. As the user continues to suck on the e-cigarette 10, this aerosol is drawn through the central passage 32 and inhaled by the user. At the same time the control electronics 22 also activates the LED 20 causing the LED 20 to light up which is visible via the translucent end cap 16 simulating the appearance of a glowing ember at the end of a conventional cigarette. As liquid present in the wick 30 is converted into an aerosol more liquid is drawn into the wick 30 from the liquid supply 33 by capillary action and thus is available to be converted into an aerosol through subsequent activation of the heating coil 28.

Some e-cigarettes are intended to be disposable and the electric power in the battery 18 is intended to be sufficient to vaporize the liquid contained within the liquid supply 33 after which the e-cigarette 10 is thrown away. In other embodiments the battery 18 is rechargeable and the liquid supply is refillable. In the cases where the liquid supply 33 is a toroidal cavity, this may be achieved by refilling the liquid supply via a refill port. In other embodiments the atomizer/liquid reservoir portion 14 of the e-cigarette 10 is detachable from the battery portion 12 and a new atomizer/liquid reservoir portion 14 can be fitted with a new liquid supply 33 thereby replenishing the supply of liquid. In some cases, replacing the liquid supply 33 may involve replacement of the heating coil 28 and the wick 30 along with the replacement of the liquid supply 33.

The new liquid supply 33 may be in the form of a cartridge having a central passage 32 through which a user inhales aerosol. In other embodiments, aerosol may flow around the exterior of the cartridge to an air inhalation port 36.

Of course, in addition to the above description of the structure and function of a typical e-cigarette 10, variations also exist. For example, the LED 20 may be omitted. The airflow sensor 24 may be placed adjacent the end cap 16 rather than in the middle of the e-cigarette. The airflow sensor 24 may be replaced with a switch which enables a user to activate the e-cigarette manually rather than in response to the detection of a change in air flow or air pressure.

Different types of atomizers may be used. Thus for example, the atomizer may have a heating coil in a cavity in the interior of a porous body soaked in liquid. In this design aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

A liquid supply 34 used in electronic smoking devices is disclosed. The liquid supply 34 has a first container member 34*a* and a second container member 34*b* complementary to the first container member to form a substantially cylindrical body.

Figure 1A:
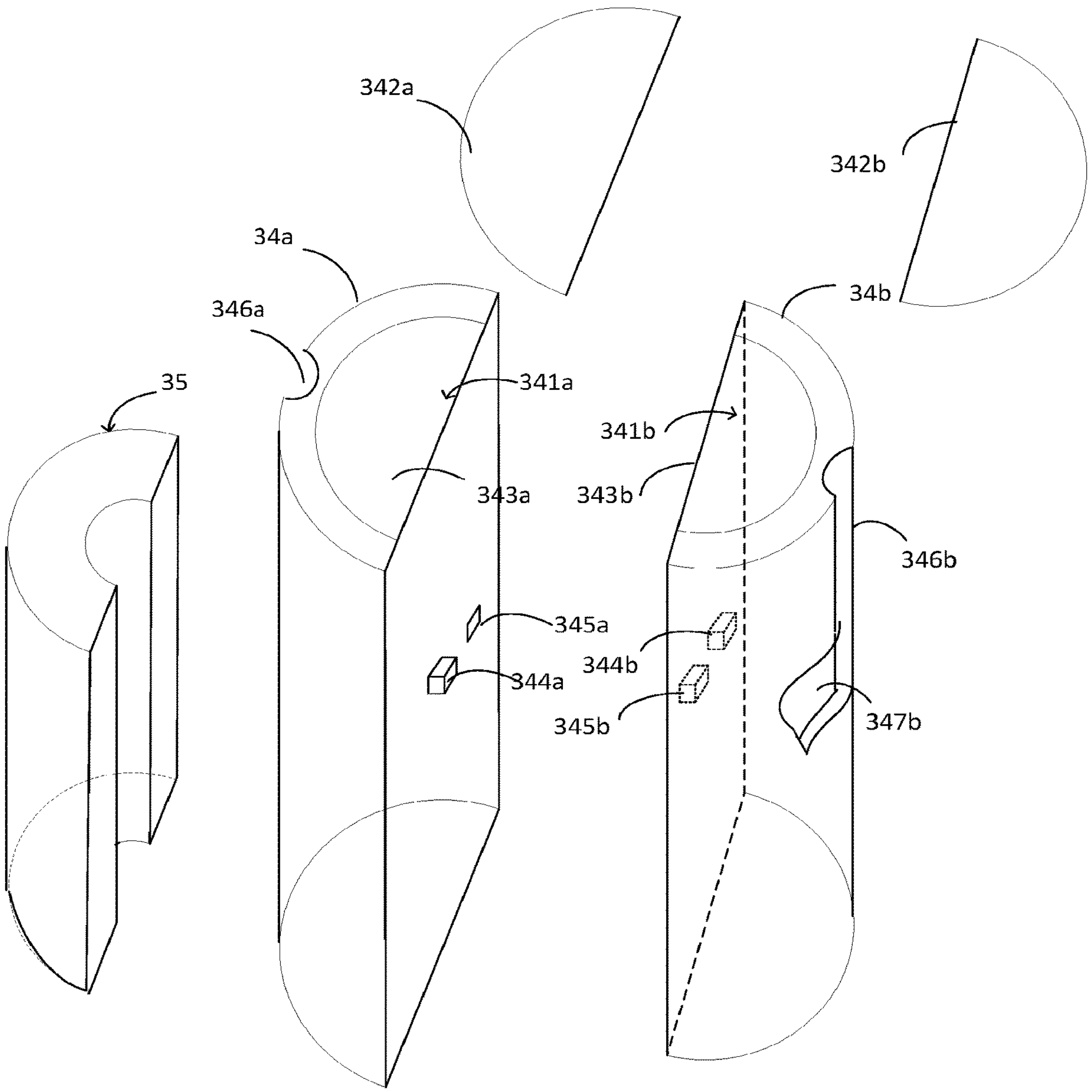
FIG. 1*a* is a perspective exploded view of a liquid supply having two container members.

Turning now to FIG. 1*a*, an alternative first container member 34*a* and the second container member 34*b* both have an outlet 341*a*, 341*b* at an end thereof. The outlets are sealed by a respective sealing members 342*a*, 342*b*, such as metal foil or paper or plastic film that can be attached by adhering, bonding, or welding. These sealing members 342*a*, 342*b* can be removed, for example by tearing off before installing the e-liquid supply 34 into the container holder of the electronic cigarette or can be pierced by at least one bayonet or spike provided within the housing of the electronic cigarette when the liquid supply is installed in the electronic cigarette in place.

Figure 1B:
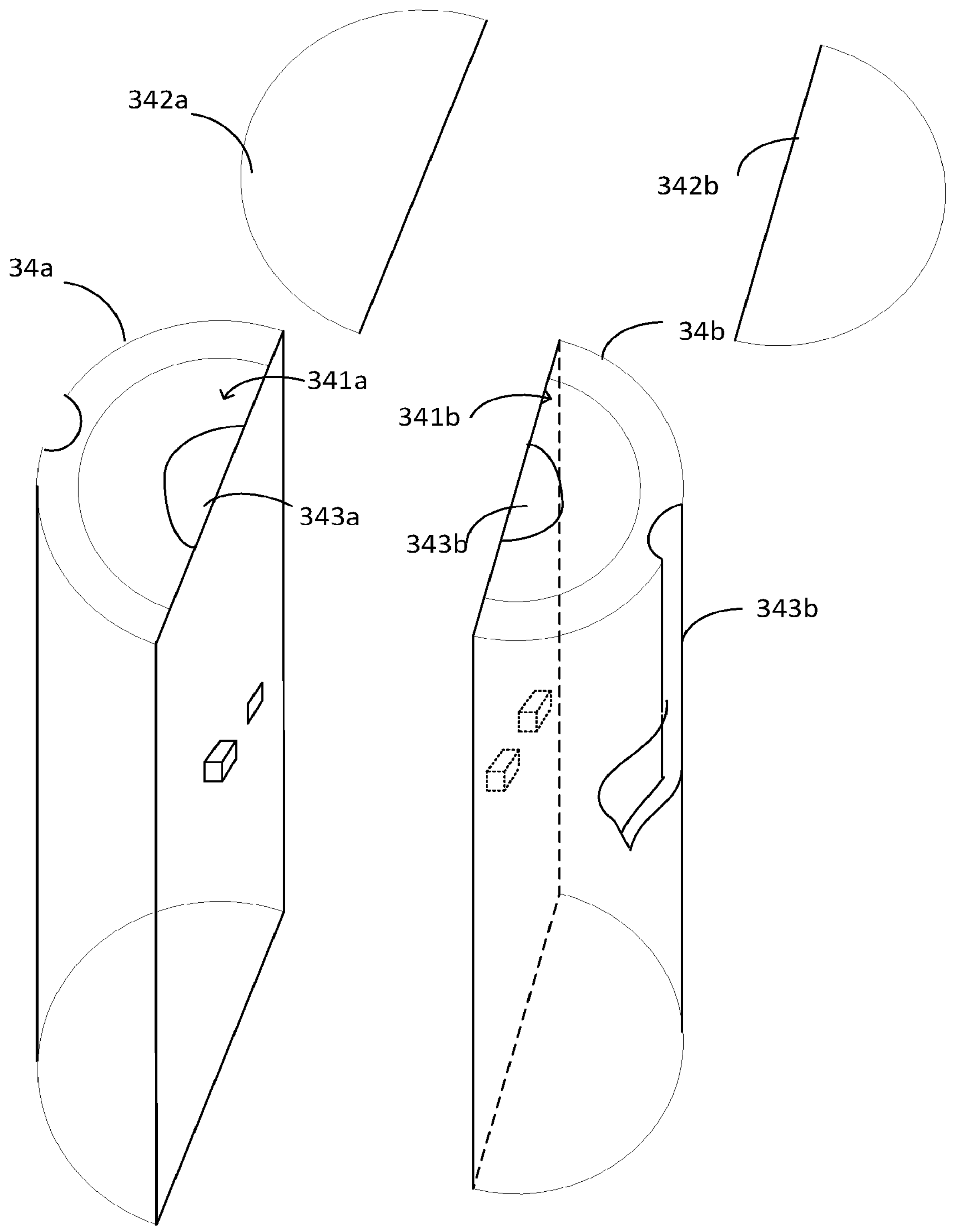
FIG. 1*b* is a perspective exploded view of a liquid supply having two container members and with aerosol channel in the center.

In one embodiment, the first container member 34*a* and the second container member 34*b* each has a cut-off portion 343*a*, 343*b*, along the longitudinal axial of the members. The cut-off portion can be for example semi-cylinder shape as shown in FIG. 1*b*. The two cut-off portions when brought together, form an aerosol channel, that is, the central passage 32, for the aerosol generated at the heating unit of the electronic cigarette to pass through.

Generally the container members are hollow and empty, so that they may be filled with bulk e-liquid. However, the first container member 34*a* and the second container member 34*b* may optionally contain wadding 35 to hold the e-liquid. The wadding can be of any shape. For example, the wadding 35 can be a semi-annular column as shown in FIG. 1*a* so that an aerosol channel can be formed by the wadding 35 and the cut off portions 343*a* and 343*b* illustrated FIG. 1*b* are no longer necessary. The e-liquid contained therein can be for example nicotine solutions with different concentrations or with different flavors.

The first and the second container members 34*a*, 34*b* can be made from translucent materials, such as translucent plastic such that the remaining content of the container member can be observed by the user. To help the user quantify the remaining amount of e-liquid in the container members, volume marks can be applied to the surface of the container members.

The wick 30 of the heater element can act as the bayonet when made from materials with sufficient stiffness. For example, the wick 30 can be made by braiding carbon fibers, glass fiber or a combination thereof. The wick 30 can also be provided with a center rod made from rigid material such as metal, plastics, and being wound by carbon fibers or glass fibers.

The first and second container members 34*a*, 34*b* are configured to fit together by a protrusion 344*a* formed on one member and an indentation 345*b* formed on the other member. The protrusion 344*a* and the indentation 345*b* can be shaped complementary to one another. As can be appreciated, the protrusion 344*a* and the indentation 345*b* are not necessarily complementary to one another, rather, a tight fit, or interference fit formed between the protrusion and the indentation would be sufficient. The protrusion 344*a* and the indentation 345*b* can be formed longitudinally along each member or traverse to the longitudinal axial of the two members. In this arrangement, the aerosol channel formed by cut off portions 343*a* and 343*b* can be arranged offset from the protrusion 344*a* and indentation 345*b* pair in case of a central aerosol channel design, otherwise the liquid supply 34 can take a peripheral aerosol channel design.

In another embodiment, more than one protrusion 344*a* and indentation 345*b* are formed on both container members 34*a*, 34*b*. The protrusions and the indentations can be arranged in any pattern, for example, the first container member 34*a* can be formed with a protrusion 344*a* and an indentation 345*a*, while the second container member 34*b* can be formed with a protrusion 344*b* and an indentation 345*b* that mate with those on the first container member. The protrusions and the indentions are preferably formed symmetrically along the longitudinal axial of the members. In the arrangement shown in FIG. 1*b*, the aerosol channel are provided along the longitudinal axial of the container formed by the two members so that the protrusions and the indentations have the same distance from the central axial.

Figure 2A:
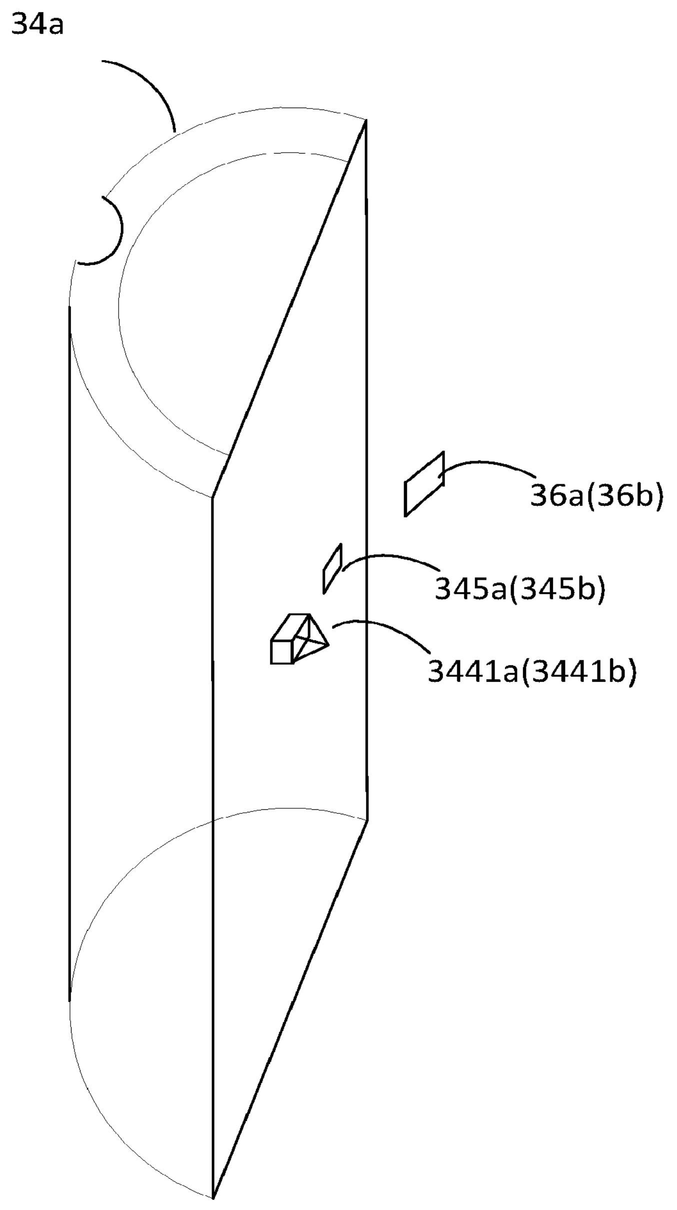
FIG. 2*a* is a perspective view of an exemplary container member and the connection mechanism thereon.

Alternatively or additionally, the indentation can be in fluid communication with the internal space of the container member it is on. In such case, the indentation 345*a*, 345*b* can be sealed by a sealing member 36*a* (36*b*) as shown in FIG. 2*a* such as a plastic film or a metal foil to avoid volatilization of e-liquid within the member. The complementary protrusion on the other container member then has a projection or bayonet 3441*a* (3441*b*) that is in fluid communication with the container member it is on and is made from wicking materials with sufficient stiffness, such as carbon fiber, glass fiber braids, cotton fibers or a combination thereof. The wicking material may be supported on or attached to a metal or plastic projection, with the projection piercing the sealing member and the wicking material then moving the liquid by capillary action. In this case the wicking material can be soft and/or flexible and without substantial stiffness. The protrusion is sized and shaped so that when the two container members are brought together, the protrusions 344*a*, 344*b* and the indentations 345*a*, 345*b* are mated and engaged to one another, the bayonet in the protrusion penetrates the sealing member on the indentation and reached the internal space of the container member that has the indentation. A fluid connection is established between the two container members through the bayonet.

Figure 2B:
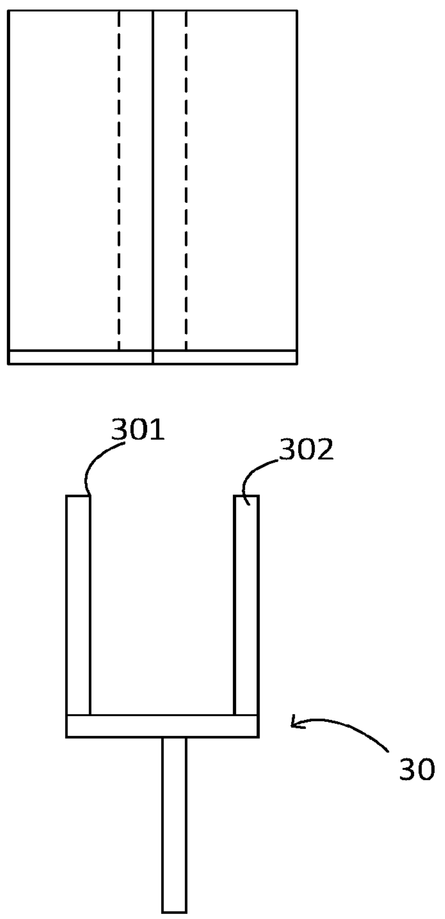
FIG. 2*b* illustrates an assembled liquid supply having two container members and a wick have two branches.

In the embodiment shown in FIG. 2*b*, the wick 30 extending from the atomizer is bifurcated into two branches 301, 302 with one branch extendable into the first container member and the other branch extendable into the second container member. The wick draws liquid from both container members through the two branches 301 and 302. A blend of liquids of different flavors from the two container members 34*a* and 34*b* can be conveyed to the atomizer for vaporization.

Figure 4:
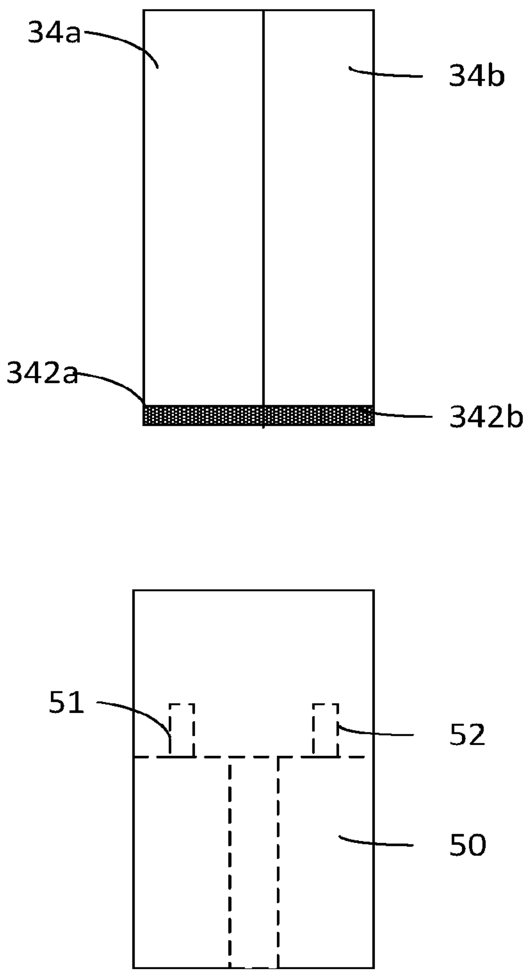
FIG. 4 is a side view of a liquid supply and an liquid guiding structure showing the bayonets within the liquid guiding structure for piecing and ripping the sealing members on the liquid supply.

In the embodiment shown in FIG. 4, a liquid guiding structure 50 is provided within the housing for conducting liquid to the atomizer. The liquid guiding structure has at least two projections or bayonets 51 and 52 to piece the seal members of the container members when the liquid supply is directed into the housing. The bayonets 51 and 52 further puncture the sealing member when the liquid supply is fixed in housing by the locking mechanism.

Referring back to FIGS. 1*a* and 1*b*, each of the container member 34*a* or 34*b* can have a first groove 346*a* or 346*b* provided longitudinally along the outer surface of the container member. The first grooves 346*a* and 346*b* can be used for guiding the container members into the electronic cigarette. For example the first groove 346*a* or 346*b* can operatively mate with guiding members, such as rails or protrusions 121 and 122 provided on the inner surface of the battery portion 12 of the electronic cigarette so that the container members 34*a* and 34*b* can be installed in the housing of the electronic cigarette by inserting them into the housing and sliding along the guiding member.

Figure 3A:
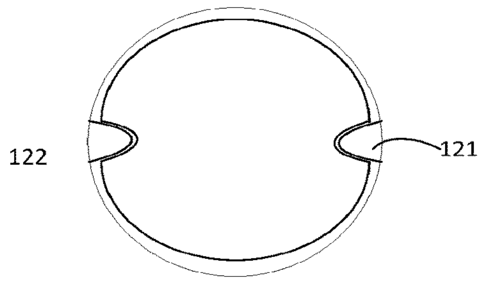
FIG. 3*a* is a top view illustrating an assembled liquid supply within the housing and the guiding structure on the liquid supply and the housing.
Figure 3B:
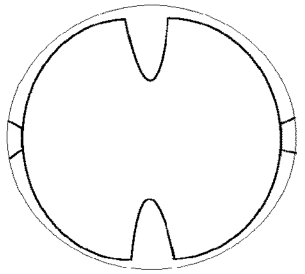
FIG. 3*b* illustrate the relative position of the assembled liquid supply within the housing.
Figure 3C:
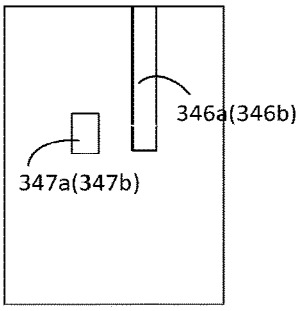
FIGS. 3*c* to 3*e* illustrate various guiding portion and locking mechanisms on the liquid supply.
Figure 3D:
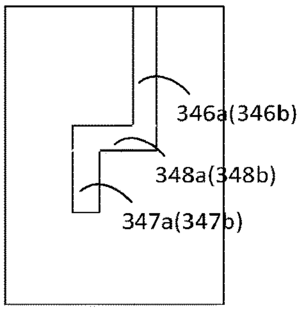

Each of the container members can have locking mechanism to fix the container members to the housing. In the embodiment shown in FIG. 3*c*, the locking mechanism can include a second groove 347*a* or 347*b* that joins with the first groove 346*a* or 346*b*. The container members can be held within the housing by rotating the container members from engaging the first groove to engaging the second groove. For container members that are made from inflexible materials, a transverse slot 348*a* or 348*b* connecting the first groove and the second groove, as shown in FIG. 3*d* can be provided by for example removing a portion of the container member between the first groove 346*a* or 346*b* and the second groove 347*a* or 347*b* so that the guiding members can move from the first groove to the second groove via the transverse slot 348*a* or 348*b*.

Figure 3E:
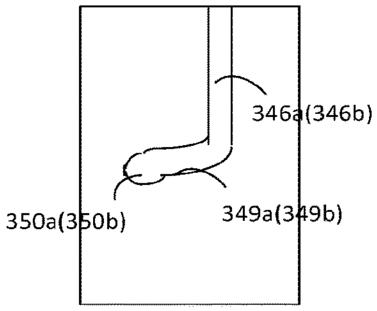

Alternatively, as shown in FIG. 3*e*, the locking mechanism can be a arcuate slot 349*a* or 349*b* extending from the first groove. The arcuate slot can have a locking profile 350*a* or 350*b* at an end of the arcuate slot. To fix the container members in the housing of the electronic cigarette, the container members are guided into the housing along the first groove and when reaches the arcuate slot the container members are turned so that the guiding members, for example the protrusions move along the arcuate slot and reaches the locking profile.

In some embodiments, the container are made from flexible materials. These container members can be held within the housing by guiding the container members into the housing and turning them to a predetermined angle so that the container members are deformed and are held by the elastic restoration force of the container members.

The number of container members can be more than two. For example, an e-liquid supply may have three container members connected to each other by above mentioned indentations and protrusions. In this case, each container member is a section of a cylinder of about 120 degrees.

Each container member can be manufactured from translucent materials such as Acrylic or other plastic and at least partially coated with a color or wrapped with a colored package to indicate the flavor of e-liquid contained with the container member.

From the foregoing, it will be appreciated that specific embodiments of the invention have been described herein for purposes of illustration, but that various modifications may be made without deviating from the scope of the invention. Accordingly, the invention is not limited except as by the appended claims.

I claim:

1. An electronic smoking device, comprising;

an atomizer and a liquid supply;

the liquid supply including only a first container directly attached to a second container, the first container having at least one protrusion on an inner-facing surface of the first container projecting into an indentation in an inner-facing surface of the second container, to directly attach the first container to the second container;

the first and second containers having liquid impermeable walls;

an opening at a first end of each of the container;

a puncturable seal on each container sealing the opening;

the inner-facing surfaces forming an aerosol channel extending from a first end of the liquid supply to a second end of the liquid supply; and an indentation seal on the indentation, the at least one protrusion piercing the indentation seal when the first and second containers are attached to each other, to establish a fluid connection between the first and second containers.

2. The electronic smoking device of claim 1 wherein the atomizer and the liquid supply are in a cylindrical housing, and the liquid supply is fixed against movement in the housing by a locking mechanism.

3. The electronic smoking device of claim 2 further comprising a guiding mechanism having a first guiding portion on at least one of the containers and a second guiding portion in the housing.

4. The electronic smoking device of claim 3 further comprising a locking mechanism locking the liquid supply to the housing by turning the liquid supply axially.

5. The electronic smoking device of claim 1 further comprising a liquid guiding structure for moving liquid from the liquid supply to the atomizer, the liquid guiding structure having at least two projections to puncture the seals.

6. The electronic smoking device of claim 1 wherein the containers comprise translucent plastic such that a remaining content of liquid in the containers can be observed by a user.

7. The electronic smoking device of claim 1 having a cylindrical aerosol channel, a first semi-circular recess in the inner-facing surface of the first container, and a second semi-circular recess in the inner-facing surface of the second container, the first and second semi-circular recesses forming the cylindrical aerosol channel.

8. The electronic smoking device of claim 7 wherein each of the first and second containers has a semi-circular outer surface.

9. An electronic smoking device, comprising:

an atomizer and a liquid supply;

a first hollow semi-circular container attached directly to a second hollow semi-circular container;

the first semi-circular container having a first flat inner surface including a first recess;

the second semi-circular container having a second flat inner surface including a second recess;

the first flat inner surface facing and parallel to the second flat inner surface;

the first recess aligned with the second recess to form an aerosol channel between the first and second hollow semi-circular containers extending from a first end of the liquid supply to a second end of the liquid supply;

each semi-circular container having a first end sealed by a sealing member, for containing liquid in the container;

each hollow semi-circular container having liquid impermeable walls;

the first container having at least one protrusion projecting into an indentation in the second container, to directly attach the first container to the second container; and an indentation seal on the indentation, the at least one protrusion piercing the indentation seal when the first and second containers are attached to each other, to establish a fluid connection between the first and second containers.

10. The electronic smoking device of claim 9 further comprising a guiding mechanism having a first guiding portion on at least one of the containers.

11. The electronic smoking device of claim 10 further comprising a locking mechanism locking the liquid supply to a housing by rotating the liquid supply axially.

12. The electronic smoking device of claim 9 further comprising a liquid guiding structure for moving liquid from the liquid supply to the atomizer, the liquid guiding structure having at least two projections to pierce the sealing members.

13. The electronic smoking device of claim 9 wherein the hollow containers comprise translucent plastic such that a remaining content of liquid in the containers can be observed by a user.

14. The electronic smoking device of claim 9 wherein the first and second recesses are semi-circular recesses forming a cylindrical aerosol channel.

* * * * *